(12) United States Patent
Makwana et al.

(10) Patent No.: US 9,175,101 B2
(45) Date of Patent: Nov. 3, 2015

(54) PRECURSOR FOR POLYOLEFIN CATALYST

(75) Inventors: Umesh Makwana, Surat (IN); Ajay Kothari, Surat (IN); Bhavesh Desai, Surat (IN); Virendrakumar Gupta, Navi Mumbai (IN)

(73) Assignee: RELIANCE INDUSTRIES LIMITED, Mumbai, Maharashtra (IN)

( * ) Notice: Subject to any disclaimer, the term of this patent is extended or adjusted under 35 U.S.C. 154(b) by 42 days.

(21) Appl. No.: 14/125,797

(22) PCT Filed: Jun. 4, 2012

(86) PCT No.: PCT/IN2012/000389
§ 371 (c)(1),
(2), (4) Date: Dec. 12, 2013

(87) PCT Pub. No.: WO2013/051006
PCT Pub. Date: Apr. 11, 2013

(65) Prior Publication Data
US 2014/0128249 A1    May 8, 2014

(30) Foreign Application Priority Data
Jun. 28, 2011    (IN) .......................... 1857/MUM/2011

(51) Int. Cl.
| | |
|---|---|
| *B01J 21/00* | (2006.01) |
| *B01J 31/00* | (2006.01) |
| *B01J 37/00* | (2006.01) |
| *B01J 37/04* | (2006.01) |
| *B01J 37/08* | (2006.01) |
| *C08F 4/64* | (2006.01) |
| *C07C 29/70* | (2006.01) |

(52) U.S. Cl.
CPC .. *C08F 4/64* (2013.01); *C07C 29/70* (2013.01)

(58) Field of Classification Search
CPC ...... B01J 2231/122; B01J 21/10; B01J 31/00; B01J 37/00; B01J 27/135; B01J 37/04; B01J 37/08
USPC .................. 502/103, 104, 107, 115, 227, 251
IPC ................ B01J 2231/122, 21/10, 31/00, 37/00, B01J 27/135, 37/04, 37/08
See application file for complete search history.

(56) References Cited

U.S. PATENT DOCUMENTS

| | | |
|---|---|---|
| 2,570,058 A | 7/1949 | Hunter |
| 3,657,361 A | 4/1972 | Lenz et al. |
| 4,442,225 A * | 4/1984 | Takitani et al. ............... 502/112 |

(Continued)

FOREIGN PATENT DOCUMENTS

| | | | |
|---|---|---|---|
| DE | 100 45 356 A1 | 3/2002 | |
| EP | 1 188 736 | * 3/2002 | ............. C07C 29/70 |

(Continued)

OTHER PUBLICATIONS

International Search Report of PCT/IN2012/000389 dated Mar. 26. 2013, 3 pages.

(Continued)

*Primary Examiner* — Patricia L Hailey
(74) *Attorney, Agent, or Firm* — Collard & Roe, P.C.

(57) ABSTRACT

The present invention provides titanium based precursor for polyolefin catalyst with desired morphology and high particle strength. The of preparation of the precursor in accordance with the present invention obviates the use of iodine.

14 Claims, 1 Drawing Sheet

(56) References Cited

U.S. PATENT DOCUMENTS

| | | | |
|---|---|---|---|
| 4,477,587 A * | 10/1984 | Band | 502/111 |
| 4,686,199 A * | 8/1987 | Tachikawa et al. | 502/104 |
| 5,077,357 A | 12/1991 | Job | |
| 6,034,189 A * | 3/2000 | Shinozaki et al. | 526/125.3 |
| 6,770,586 B2 * | 8/2004 | Tashino et al. | 502/127 |
| 6,982,237 B2 * | 1/2006 | Wagner et al. | 502/125 |
| 7,737,069 B2 * | 6/2010 | Tanase et al. | 502/102 |
| 8,633,124 B2 * | 1/2014 | Gupta et al. | 502/111 |
| 2001/0012908 A1 * | 8/2001 | Tanase et al. | 568/851 |
| 2002/0032354 A1 | 3/2002 | Standke et al. | |
| 2009/0112027 A1 | 4/2009 | Dietz et al. | |
| 2009/0148702 A1 | 6/2009 | Dietz et al. | |
| 2010/0298509 A1 * | 11/2010 | Kim et al. | 526/124.3 |
| 2013/0211022 A1 * | 8/2013 | Gupta et al. | 526/124.1 |

FOREIGN PATENT DOCUMENTS

| | | | |
|---|---|---|---|
| EP | 1 188 736 A1 | 3/2002 | |
| JP | 2002114724 A | 4/2002 | |
| WO | 2005/044873 A1 | 5/2005 | |
| WO | 2006/033512 A1 | 3/2006 | |
| WO | 2009/130707 A2 | 10/2009 | |
| WO | 2012/007963 A2 | 1/2012 | |
| WO | 2013/051006 * | 4/2013 | C07C 29/70 |

OTHER PUBLICATIONS

Tanase et al., New Synthesis Method Using Magnesium Alkoxides as Carrier Materials for Ziegler-Natta Catalysts with Spherical Morphology, Macromol. React. Eng., 2008, pp. 233-239.

Tanase et al., Applied Catalysis A: General, Particle growth of magnesium alkoxide as a carrier material for polypropylene polymerization catalyst, 350, 2008, pp. 197-206.

* cited by examiner

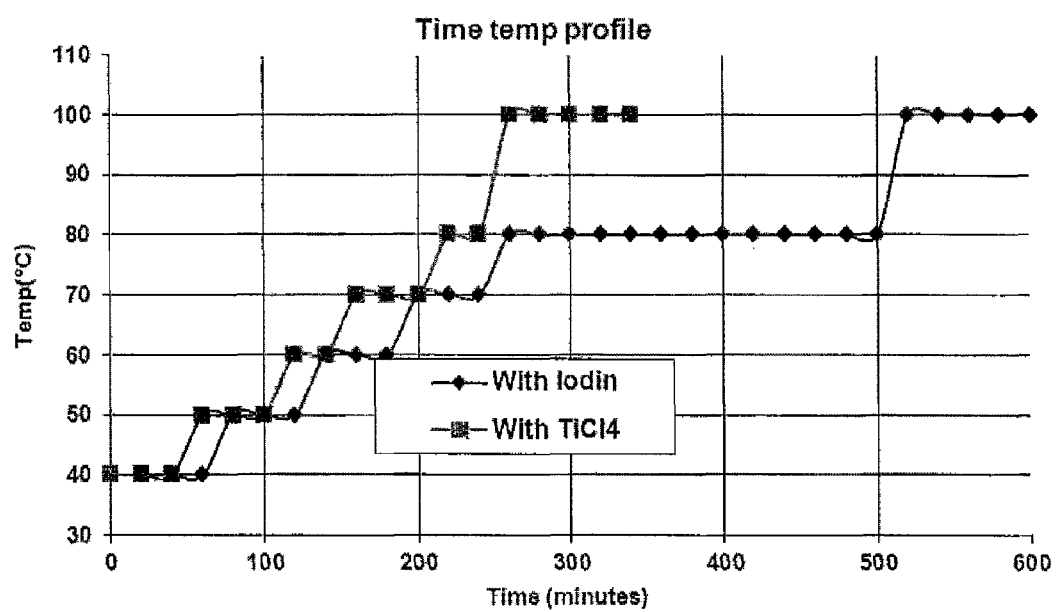

PRECURSOR FOR POLYOLEFIN CATALYST

CROSS REFERENCE TO RELATED APPLICATIONS

This application is the National Stage of PCT/IN2012/000389 filed on Jun. 4, 2012 which claims priority under 35 U.S.C. §119 of Indian Application No. 1857/MUM/2011 filed on Jun. 28, 2011, the disclosures of which are incorporated by reference. The international application under PCT article 21(2) was published in English.

FIELD OF INVENTION

The present invention relates to a process for preparation of a precursor for a catalyst.

More particularly the present invention relates a process for preparation of a magnesium based precursor for a polyolefin catalyst.

BACKGROUND

The commercially available magnesium alkoxides are synthesized by the reaction of magnesium metal with alcohols in the presence of reaction initiators like iodine. For example, WO2005/044873 discloses a method for synthesizing spherical magnesium alkoxide particles by reacting magnesium with an alcohol mixture at a temperature below the boiling point of the mixture using $I_2$ as a reaction initiator.

There are several drawbacks associated with the method as provided in the aforesaid PCT application. The spherical magnesium alkoxide particles synthesized by such method are frangible and they do not retain their morphology or particle size during the synthesis of Ziegler Natta procatalyst, especially when the procatalyst synthesis is carried out on a plant scale. Furthermore, a resin produced using the method reported in WO2005/044873 exhibits low resin bulk density which in turn hampers the plant throughput.

A method which attempts to overcome the problems mentioned above has been disclosed in U.S. Pat. No. 5,077,357. It employs dissolution and re-precipitation methodology to incorporate chlorine and the titanium atoms in the matrix of the precursor. In accordance with the method disclosed by U.S. Pat. No. 5,077,357, magnesium alkoxide is dissolved in a halo-hydrocarbon solvent by heating a mixture of magnesium alkoxide, titanium tetra chloride, titanium tetra ethoxide, alcohol, and a phenol derivative at an elevated temperature and the re-precipitation is carried out by the removal of alcohol from the system. The solid semi spherical particles magnesium particles are separated by filtration.

Provided herein below is a brief summary of the known processes wherein iodine has been used as an initiator in the synthesis of the magnesium alkoxide based precursor.

A method for producing the morphology controlled magnesium alkoxide with high mechanical strength and controlled particles size precursor which employs iodine is disclosed in WO2009/130707. It involves the activation of the magnesium metals by iodine to react with a mixture of alcohols at a controlled rate.

A method for synthesis which employs magnesium alkoxide as a carrier material for preparing Ziegler Natta Catalysts with Spherical Morphology has been disclosed in Macromol. React Eng., 2(2008)233-239. It employs Metal halides (MnCl2, FeCl2, CoCl2 and ZnCl2) to synthesize Magnesium ethoxide in the presence of iodine.

Another article, Applied Catalysis A: General 350(2008) 197-206 "Particle growth of magnesium alkoxide as a carrier material for polypropylene polymerization catalyst" provides the details of a process that employs Iodine as a reaction initiator. This article also provides the details of the mechanism by which particles are formed (agglomerates of primary particles) on the surface of magnesium metal. Also, disclosed in this article is the replication of morphology from precursor to catalyst to polymer.

Apart from the abovementioned references, methods for synthesis of the magnesium alkoxide precursor using halogen initiators and activators are taught in US 2009/0112027, US2009/0233793, US2009/0148702, U.S. Pat. No. 5,077,357 and WO/2009/130707.

The drawback of the precursor prepared through the iodine activator is that its particle strength is low and therefore it is prone to breakage. This results in the formation of fines during catalyst synthesis. As a result a polymer obtained through the catalyst also contains very high level of fines which causes frequent choking problems in a commercial plant. Furthermore, the precursor prepared through iodine activator form iodine compounds which remain with the precursor. This adversely affects the performance of the catalyst.

In view of the above, there is therefore exists a need for a method to synthesize a magnesium alkoxide based precursor with high particle strength that overcomes the drawbacks associated with the prior art.

OBJECTS

An object of the invention is to provide a method for preparation of a morphologically controlled catalyst precursor with high particle strength.

Another object of the invention is to provide a method that improves the precursor strength without contaminating the alkoxide matrix of the precursor.

Still another object of this invention is to provide an energy efficient method for preparation of the precursor.

A further object of the invention is to prepare a precursor in an energy efficient manner.

A still further object of the present invention is to provide a supported Ziegler-Natta catalyst with controlled morphology with improved particle strength.

SUMMARY

In accordance with the present invention there is provided a method for synthesis of a catalyst precursor with controlled morphology; said method comprising the following steps:

reacting predetermined amount of magnesium metal particles with an alcohol at a temperature ranging between 35° C. to 50° C. under agitation to obtain a reaction mixture;

adding predetermined amount of titanium tetrachloride to the reaction mixture leading to the evolution of hydrogen from the reaction mixture;

heating the reaction mixture gradually till the temperature of the mixture reaches to a reflux temperature and refluxing the reaction mixture till the time the evolution of hydrogen from the mixture stops completely;

increasing the temperature of the reaction mixture to about 100° C. to remove the excess alcohol in the reaction mixture to obtain a precursor and subjecting the same to drying.

Typically, the alcohol is selected from the group consisting of $C_1$-$C_{12}$ aliphatic alcohols and any mixture thereof.

Preferably, the alcohol is selected from the group consisting of methyl alcohol, ethyl alcohol, propyl alcohol, butyl alcohol, isopropyl alcohol and any mixture thereof.

Typically, the proportion of the metal, the alcohol and titanium tetrachloride, when expressed in terms of moles, is in the range between 0.5:2:0.001 to 1:6:0.15.

In accordance with a preferred embodiment of the present invention, the proportion of the metal, the alcohol and titanium tetrachloride, when expressed in terms of moles is 1:5:0.03.

In one embodiment, the method of the present invention further comprises preparing a supported Ziegler-Natta catalyst from the precursor; wherein preparing the catalyst comprises reacting the precursor with titanium tetrachloride optionally in the presence of an electron donating species to the obtain a catalyst, treating the catalyst with a titanium halide again and washing the same with a hydrocarbon solvent to remove the free titanium.

In accordance with one embodiment of the present invention, the electron donating species is ethyl benzoate and the catalyst prepared is a mono-ester catalyst.

In accordance with another embodiment of the present invention, the electron donating species is di iso butyl phthalate and the catalyst prepared is a di-ester catalyst.

Typically, the hydrocarbon solvent is selected from the group consisting of aromatic or aliphatic hydrocarbons and any mixture thereof.

Preferably, the hydrocarbon solvent is preferably selected from the group consisting of chlorobenzene, toluene, ortho-chloro toluene, $C_1$-$C_{14}$ aliphatic hydrocarbon and any mixture thereof.

Typically, the reaction mixture containing the precursor, titanium halide and an electron donating species is heated up to 100° C. within 15 minutes and the temperature is kept constant for about 30 minutes.

In another aspect of the present invention there is provided a supported Ziegler-Natta catalyst with controlled morphology that is essentially devoid of iodine.

Typically, sphericity value of the catalyst is in the range of 0.80 to 0.90. Typically, the particle breakage index of the catalyst is in the range of 0.85 to 0.97.

DETAILED DESCRIPTION

The morphology of the precursors is a function of process parameters like the rate of reaction, temperature and the types of alcohols used. The morphology of final polyolefin is a replication of catalyst and the catalyst morphology is replication of precursor morphology.

The present invention therefore provides a method for preparation of a precursor with desired morphology and high particle strength that does not involve contamination by iodine.

The method in accordance with the present invention overcomes the drawbacks associated with the prior art process by employing $TiCl_4$ as a magnesium metal activator. This increases the strength of the particles and avoids the contamination of the catalyst. Furthermore, the residue of titanium in the precursor does not affect the performance of the catalyst as it is one of the catalyst components of the catalyst system.

In accordance with the method for preparation of a precursor with controlled morphology in accordance with the present invention a predetermined quantity of magnesium metal is introduced to an alcohol. Alcohol that is used in accordance with the method of the present invention is selected from the group consisting of $C_1$-$C_{12}$ aliphatic alcohols and any mixture thereof. Preferably, the alcohol is selected from the group consisting of methyl alcohol, ethyl alcohol, propyl alcohol, butyl alcohol, isopropyl alcohol and mixture thereof.

The addition of magnesium particles to the alcohol is carried out gradually under agitation at a temperature ranging between 35° C. to 50° C. Preferably, the magnesium metal particles are added to the alcohol at a temperature of about 40° C. under continuous agitation. The agitator speed is maintained in range of about 150 rpm to about 400 rpm. Preferably, the speed of the agitator is maintained at 300 rpm.

After about 20 minutes, pre-determined amount of titanium tetrachloride is added to the reaction mixture. The introduction of titanium tetrachloride, which acts as an initiator; results in evolution of hydrogen from the reaction mixture. The evolution of hydrogen indicates the commencement of the reaction. The rate of the reaction is monitored by observing the rate of evolution of the hydrogen from the reaction mixture.

The proportion of the reactants (when expressed in terms of moles), magnesium metal, ethanol and titanium tetrachloride typically ranges between 0.5:2:0.001 to 1:6:0.15. Preferably, the proportion of the metal, alcohol and titanium tetra chloride is 1:5:0.03.

The temperature of the reaction mixture is increased in a stepwise manner. The temperature is increased only when the effervescence of hydrogen stops indicating the stoppage of the reaction. The temperature of the reaction mixture is increased in a stepwise manner till the reflux temperature of the reaction mixture. Typically, the reflux temperature of the mixture ranges between 70° C. to about 90° C., preferably about 80° C. The time period for reaching the reflux temperature is typically ranges between 3.5 to about 4 hours.

After the temperature of the mixture reaches to its reflux temperature, the reaction mixture is refluxed for a period ranging between 40 minutes to 120 minutes. In accordance with one embodiment of the invention, the reflux temperature is 80° C. and the time period for which the reaction mixture is refluxed is 60 minutes. Once the hydrogen evolution is stopped at the reflux temperature of the reaction mixture, the temperature of the reaction mixture is increased to about 100° C. The excess of alcohol is evaporated. Alternatively, the excess of ethanol is condensed under Nitrogen atmosphere. The solid precursor is subjected to drying at a temperature of about 60° C. to about 130° C. under the flow of nitrogen till to obtain a free flowing powder. The final product is collected and weighed and the chemical composition is determined.

In another aspect, the present invention also provides a process for preparation of monoester and diester catalysts using the precursor in accordance with the present invention.

The method for synthesis of supported Ziegler-Natta (ZN) catalyst for propylene polymerization from titanium based magnesium alkoxide precursor prepared in accordance with the method of this invention comprises reacting titanium based precursor with a mixture of titanium halide and halogenated aromatic solvent optionally in the presence of electron donating species.

Typically, the electron donating species are selected from the group consisting of monoester and diester aromatic moieties. Preferable the electron donating species is at least one selected from the group consisting of ethyl benzoate and di iso butyl phthalate. Typically, the reaction is carried out between 80° C. to 110° C. for a time period ranging between one to two hours. The catalyst obtained is again treated with titanium halide and washed with hydrocarbon solvent until all the free titanium is removed. Typically, the hydrocarbon solvent is selected from the group consisting of aromatic or aliphatic hydrocarbons and mixture thereof. Preferably, the hydrocarbon solvent is selected from the group consisting of chlorobenzene, toluene, ortho-chloro toluene, $C_1$-$C_{14}$ aliphatic hydrocarbon and any mixture thereof.

In still another aspect of the present invention, there is a provided a supported Ziegler-Natta catalyst with controlled morphology that is essentially devoid of iodine prepared in accordance with the method as described herein above.

Typically, the sphericity value of supported Ziegler-Natta catalyst with controlled morphology prepared in accordance with the present invention is in the range of 0.80 to 0.90. Typically, the particle breakage index of the catalyst prepared in accordance with the present invention is in the range of 0.85 to 0.97.

The catalyst produced in accordance with the method of the present invention is used for olefin polymerization to produce regular shaped polymer particles.

In still another aspect of the present invention there is provided a method for synthesis of supported Ziegler-Natta (ZN) catalyst for olefin polymerization from the titanium based magnesium alkoxide precursor of the present invention.

The method for preparation of the olefin catalyst using the precursor of the present invention comprises reacting the precursor with a mixture of titanium halide and a halogenated aromatic solvent.

Typically, the reaction is carried out between 80° C. to 110° C. for a time period ranging between one to two hours. The catalyst obtained is again treated with titanium halide and washed with hydrocarbon solvent until all the free titanium is removed. Typically, the hydrocarbon solvent is selected from the group consisting of aromatic or aliphatic hydrocarbons and mixture thereof. Preferably, the hydrocarbon solvent is selected from the group consisting of chlorobenzene, toluene, ortho-chloro toluene, $C_1$-$C_{14}$ aliphatic hydrocarbon and any mixture thereof.

The invention will now be described with the help of following non-limiting examples:

Example 1

Synthesis of a Titanium Tetrachloride Based Magnesium Alkoxide Precursor in Accordance with the Present Invention In a three necked reactor 150 ml of alcohol (ethanol) was taken. 10 gm of Mg metals were added at elevated (40° C.). The speed of the agitator was maintained at 300 rpm. Table 1 provided herein below provides the particle size distribution of the magnesium particles.

TABLE 1

Particle size of Magnesium Metal used

| Mesh No. | Micron Size | Tare Wt. gm | Gross Wt. gm | Net Wt. gm | % Retention on |
|---|---|---|---|---|---|
| 40 | 400 | 0.7313 | 0.7338 | 0.0025 | 0.12 |
| 60 | 250 | 0.724 | 1.5385 | 0.8145 | 40.59 |

TABLE 1-continued

Particle size of Magnesium Metal used

| Mesh No. | Micron Size | Tare Wt. gm | Gross Wt. gm | Net Wt. gm | % Retention on |
|---|---|---|---|---|---|
| 80 | 177 | 0.6739 | 1.5099 | 0.836 | 41.66 |
| 100 | 149 | 0.6668 | 0.8434 | 0.1766 | 8.8 |
| 140 | 105 | 0.5276 | 0.6537 | 0.1261 | 6.28 |
| 200 | 74 | 0.5023 | 0.5511 | 0.0488 | 2.43 |
| PAN | PAN | 0.8347 | 0.8369 | 0.0022 | 0.11 |
| | | | | 2.0067 | |
| | ACTUAL Wt. = | | | 99.98 | 100 |
| | <140u = | | | 2.54 | |
| | APS = | | | 252 | |

After 20 minutes a calculated quantity of Titanium tetrachloride was added to it and immediately the evolution of $H_2$ with very high effervesces was observed which indicated the start of the reaction. The exact process parameters are shown in the following Table-2.

TABLE 2

Process Parameters

| Experiment Detail | Mg metals Qty (gm) | TiCl$_4$ Qty (ml) | Ethanol Qty (ml) | Temp. (° C.) From-To | Total Time (Hrs) | RPM | Moles of Mg | Moles of TiCl$_4$ | Moles of Ethanol |
|---|---|---|---|---|---|---|---|---|---|
| Precursor through TiCl$_4$ | 10 | 0.3 | 150 | 40-100 | 6 | 300 | 0.41 | 0.003 | 2.61 |

Visually the rate of hydrogen evolution was monitored and the temperature was increased in a step wise manner from 40° C. to 80° C. During this range, whenever the hydrogen evolution stopped, the temperature was increased to keep the reaction going. Time temperature profile of the reaction is shown in FIG. 1.

The reaction mixture was refluxed for one hour at 80° C. and once the hydrogen evolution stopped, the temperature was further increased to 100° C. to remove un-reacted ethanol from the reactor. The precursor thus obtained was subjected to drying at about 130° C. under the flow of nitrogen obtain a free flowing powder.

Comparative Example A

Precursor was also synthesized by using Iodine as an initiator as reported in the prior art. Particle size distribution of the Magnesium metal used for synthesis of the prior art precursor was same as provided in Table 1. The process employed for the synthesis of the prior precursor was same as provided in example 1 except that Iodine was used as the initiator. The process parameters for the synthesis of the prior art precursor are provided below in Table 3.

TABLE 3

| Experiment Detail | Mg metals Qty (gm) | $I_2$ Qty (ml) | Ethanol Qty (ml) | Temp. (°C.) From-To | Total Time (Hrs) | RPM | Moles of Mg | Moles of $I_2$ | Moles of Ethanol |
|---|---|---|---|---|---|---|---|---|---|
| Precursor through $TiCl_4$ | 10 | 0.32 | 150 | 40-100 | 10 | 300 | 0.41 | 0.003 | 2.61 |

The precursor prepared in accordance with the present invention and the prior art precursor were used for preparing catalysts using ethyl benzoate as internal electron donating species. The catalysts thus prepared were evaluated by carrying out propylene polymerization.

Example 2

Mono-Ester Catalyst Synthesis Using Titanium Tetrachloride Based Magnesium Alkoxide Precursor Prepared in Accordance with the Present Invention

(A) A 500 ml three necked jacketed glass reactor was connected with a mechanical stirrer and a condenser. 10 gm of the precursor of the present invention was added in the reactor at 40° C.

(B) 230 ml of a mixture of $TiCl_4$ and chlorobenzene (50/50% by volume) was charged to the reactor under inert atmosphere at 300 RPM.

(C) After 10 minutes, 4.5 ml of ethyl benzoate was added and the temperature was increased up to 100° C. (by hot oil circulator) within 15 minutes and then the reaction mixture was hold for 30 minutes at 100° C.

(D) The stirring was stopped to settle down the solid content for 15 minutes. The supernatant liquid was siphoned off and again 230 ml of a mixture of $TiCl_4$ and chlorobenzene (50/50% by volume) was charged to the reactor under inert atmosphere at 300 RPM and the reaction mixture was hold for 60 minutes.

(E) Step-D was repeated with the addition of 0.8 ml of benzoyl chloride and the reaction mixture was hold for 60 minutes at 100° C.

(F) The stirring was stopped and the solid was allowed to settle down for 15 minutes. The supernatant liquid was siphoned off and the solid catalyst was washed four times with hexane.

(G) The hexane slurry of catalyst was collected for the propylene polymerization and the remaining was dried for the other characteristics evaluation.

The slurry polymerization performance of catalysts was carried out by using triethyl aluminium as co catalyst (mole ratio, Al/Ti=250) and para ethoxy ethyl benzoate as external donor (mole ratio Al/D=5). Hexane (2.0 L) was used as polymerization solvent in 5.0 L stainless steel reactor at 400 rpm and 5.0 kg/cm2 propylene pressure for 60 minutes at 70° C. temperature. 240 mL of hydrogen was injected in the reactor before the insertion of propylene. The polymer amount obtained was measured and the activity of catalyst was determined. The polymer was also characterized for isotacticity and melt flow index at 230° C.

Comparative Example B

Another monoester-catalyst was synthesized using the same method as above except that the prior art precursor was used as the starting material.

Test Data:

The titanium tetrachloride based magnesium alkoxide precursor of the present invention and the prior art precursor and the respective catalysts prepared there from were evaluated.

The amount of the chemical species (Ti, Mg, Cl and Ethoxy) in the precursor was determined by UV spectroscopy, titration method and gas chromatography respectively. The iodine content in the precursor was measured by energy dispersive x-ray analysis (EDXA).

The morphology was determined for particles size and size distribution by laser diffraction technique. The size of particles was measured for D10, D50, D90 and mean in microns. The distribution span is a measure of morphology control. The distribution span is defined as per the following formula:

$$\text{Span} = \frac{D_{90} - D_{10}}{D_{50}}$$

Thus, the lower value indicates narrow particle size distribution and is indicative of good control over the morphology of particles.

The over all morphology and sphericity (or circularity) is determined by scanning electron microscopy. The sphericity of particles is calculated by measuring the area covered by a particle under the image through a software and the value is put in the following formula to calculate the circularity (or sphericity)

$$\text{Circularity} = 4\pi \frac{\text{Area}}{\text{Perimeter}^2}$$

Similarly many particles images were considered for the above calculation and then the average of them was taken as over all sphericity of the materials.

The improvement in mechanical strength was measured through breakage ratio (particle breakage index) which is defined as the ratio of mean particle size of catalyst to the precursor used as shown by the following formula.

$$\text{Particle breakage index} = \frac{\text{Mean particle size of the catalyst}}{\text{Mean particle size of the Precursor}}$$

As the value is nearer to 1 the particle breakage is less and hence higher mechanical strength.

The evaluation data generated after carrying out the above tests is provided herein below in Table No 4.

TABLE NO 4

Catalyst characteristics and polymerization performance of monoester catalysts

| Example No | Chemical composition (wt %) | | | | | Mean PSD (μm) | Particle breakage index | Circularity | Activity (Kg PP/gm Cat) | Isotactic Index (wt %) | MFI gm/10 min |
|---|---|---|---|---|---|---|---|---|---|---|---|
| | Ti | Mg | Cl | EB | OEt | | | | | | |
| Comparative Example B | 2.8 | 19.5 | 60.5 | 15.5 | 0.3 | 25 | 0.71 | 0.72 | 5.5 | 96.8 | 3.5 |
| 2 | 2.9 | 20.5 | 60 | 15 | 0.2 | 35 | 0.92 | 0.86 | 6.0 | 96.9 | 3.3 |

Example 3

Synthesis of a Diester Catalyst Using Titanium Tetrachloride Based Magnesium Alkoxide Precursor in Prepared in Accordance with the Present Invention The process for synthesis of diester catalyst is similar to the process for preparing monoester catalyst as mentioned above in Example 2. Following modifications in the monoester catalyst process are done for synthesizing the diester catalyst.

(1) Di-isobutyl phthalate was used as the internal electron donating species [in place of ethyl benzoate] and (2) the reaction temperature was 110° C. [instead of 100° C.] for all the process steps.

Comparative Example C

Another di-ester-catalyst was synthesized using the same method as above except that the prior art precursor was used as the starting material.

The polymerization performance was evaluated by replacing the external donor as cyclohexyl methyl dimethoxy silane instead of paraethoxy ethyl benzoate with the mole ratio (Al/D=30) and the polymerization was carried out for 120 minutes.

The catalyst characteristics and polymerization performance data for the diester catalysts prepared in Example 3 and Comparative Example C is provided herein below in Table 5.

Performance of Titanium Tetrachloride Based Magnesium Alkoxide Precursor for Polyethylene Example 4

Catalyst Synthesis Using Titanium Tetrachloride Based Magnesium Alkoxide Precursor Prepared in Accordance with the Present Invention (A) A 500 mL three necked jacketed glass reactor was connected with a mechanical stirrer and a condenser. 10 gm of the precursor of the present invention was added in the reactor at 40° C.

(B) 230 mL of a mixture of $TiCl_4$ and chlorobenzene (50/50% by volume) was charged to the reactor under inert atmosphere at 300 RPM.

(C) The stirring was stopped to settle down the solid content for 15 minutes. The supernatant liquid was siphoned off and again 230 ml of a mixture of $TiCl_4$ and chlorobenzene (50/50% by volume) was charged to the reactor under inert atmosphere at 300 RPM and the reaction mixture was hold for 60 minutes.

(D) The stirring was stopped and the solid was allowed to settle down for 15 minutes. The supernatant liquid was siphoned off and the solid catalyst was washed four times with hexane.

(E) The hexane slurry of catalyst was collected for the ethylene polymerization and the remaining was dried for the other characteristics evaluation.

TABLE 5

Catalyst characteristics and polymerization performance of Diester catalysts

| Example No | Chemical composition (wt %) | | | | | Mean PSD (μm) | Particle breakage index | Circularity | Activity (Kg PP/gm Cat) | Isotactic Index (wt %) | MFI gm/10 min |
|---|---|---|---|---|---|---|---|---|---|---|---|
| | Ti | Mg | Cl | DIBP | OEt | | | | | | |
| Comparative Example C | 2.9 | 18.9 | 59.5 | 14 | 0.3 | 22 | 0.63 | 0.72 | 8.5 | 98.5 | 2.5 |
| 3 | 2.9 | 19.5 | 60.2 | 13.5 | 0.2 | 33 | 0.92 | 0.86 | 10.5 | 98.2 | 3.0 |

The catalyst performance test for ethylene polymerization was carried in 400 mL stainless steel reactor at high pressure in hexane slurry. Triethyl aluminium was used as co catalyst (mole ratio, Al/Ti=80=5). The polymerization was performed using 150 mL of hexane as polymerization solvent at 400 rpm and 5.0 kg/cm2 ethylene pressure was maintained for 120 minutes at 70° C. temperature. 80 mL of hydrogen was injected in the reactor before the insertion of ethylene. The polymer amount obtained was measured and the activity of catalyst was determined. The polymer was also characterized for morphology and melt flow index at 190° C.

Comparative Example D

Another catalyst was synthesized using the same method as above except that the prior art precursor was used as the starting material.

The catalyst characteristics and polymerization performance data for the diester catalysts prepared in Example 4 and Comparative Example D is provided herein below in Table 6.

TABLE 6

Catalyst characteristics and polymerization performance for ethylene

| Example No | Chemical composition (wt %) | | | | Mean PSD (μm) | Particle breakage index | Circularity | Activity (Kg PE/gm Cat) | MFI gm/10 min |
|---|---|---|---|---|---|---|---|---|---|
| | Ti | Mg | Cl | OEt | | | | | |
| Comparative Example D | 5.2 | 21 | 68 | 4.5 | 25 | 0.71 | 0.75 | 4.8 | 3.5 |
| 4 | 4.3 | 22 | 70 | 3.2 | 32 | 0.84 | 0.85 | 5.6 | 3.8 |

1. Mechanical Strength of Particles:

The catalysts made from the titanium tetrachloride based magnesium alkoxide precursor prepared in accordance with the present invention were found to have lower breakage ratio (Table 4 and 5) as compared to the catalysts made from the prior art precursor in case of monoester as well as the di-ester catalysts. Thus, the titanium tetrachloride based magnesium alkoxide precursor of the present invention possesses higher particle strength.

2. Morphology of Particles:

Titanium tetrachloride based magnesium alkoxide precursor prepared in accordance with the present invention precursor showed lower value for the span of particle size as compared to the prior art precursor and it showed better control over particle size distribution. Similarly the sphericity value for the precursor prepared in accordance with the present invention was found to be higher as compared with the sphericity value of the prior art precursor. The high sphericity value is indicative of the better control over morphology.

3. Polymerization Activity:

Higher catalytic activity was observed in case of the catalysts made from the precursor of the present invention on account of the absence of iodine from the catalyst.

Technical Advancement:

The precursor of the present invention is devoid of iodine and therefore the catalyst made there from precludes the possibility of contamination by iodine compounds. The present invention also provides a precursor with high particle strength which limits the formation of fines. This in turn avoids the choking of the reactors thereby improving the efficiency and productivity.

Unlike the prior art process, the method of the present invention is simple since it does not involve dissolution or re-precipitation. The present invention provides a single step method to incorporate titanium and chlorine atom in the matrix of magnesium alkoxide. Retention of the catalyst morphology on account of the high particle strength of the precursor helps in manufacturing polymers having good morphology.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

While considerable emphasis has been placed herein on the specific ingredients of the preferred formulation, it will be appreciated that many additional ingredients can be added and that many changes can be made in the preferred formulation without departing from the principles of the invention. These and other changes in the preferred formulation of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A method for synthesis of a catalyst precursor with controlled morphology; said method comprising the following steps: reacting predetermined amount of magnesium metal particles with an alcohol at a temperature ranging between 35° C. to 50° C. under agitation to obtain a reaction mixture; adding a predetermined amount of titanium tetrachloride to the reaction mixture leading to the evolution of hydrogen from the reaction mixture; heating the reaction mixture gradually until the temperature of the mixture reaches to a reflux temperature and refluxing the reaction mixture until the time the evolution of hydrogen from the mixture stops completely; increasing the temperature of the reaction mixture to about 100° C. to remove the excess alcohol in the reaction mixture to obtain a precursor and subjecting the same to drying.

2. The method as claimed in claim 1, wherein the alcohol is selected from the group consisting of C1-C12 aliphatic alcohols and any mixture thereof.

3. The method as claimed in claim 1, wherein the alcohol is preferably selected from the group consisting of methyl alcohol, ethyl alcohol, propyl alcohol, butyl alcohol, isopropyl alcohol and any mixture thereof.

4. The method as claimed in claim 1, wherein the proportion of the metal, the alcohol and titanium tetrachloride, when expressed in terms of moles, is in the range between 0.5:2:0.001 to 1:6:0.15.

5. The method as claimed in claim 1, wherein the proportion of the metal, the alcohol and titanium tetrachloride, is 1:5:0.03.

6. The method as claimed in claim 1, further comprising preparing a supported Ziegler-Natta catalyst from the precursor; wherein preparing the catalyst comprises reacting the precursor with titanium tetrachloride optionally in the presence of an electron donating species to the obtain a catalyst, treating the catalyst with a titanium halide again and washing the same with a hydrocarbon solvent to remove the free titanium.

7. The method as claimed in claim 6, wherein the electron donating species is ethyl benzoate and the catalyst prepared is a mono-ester catalyst.

8. The method as claimed in claim 6, wherein the electron donating species is di iso butyl phthalate and the catalyst prepared is a di-ester catalyst.

9. The method as claimed in claim 6, wherein the hydrocarbon solvent is selected from the group consisting of aromatic or aliphatic hydrocarbons and any mixture thereof.

10. The method as claimed in claim 6, wherein the hydrocarbon solvent is preferably selected from the group consisting of chlorobenzene, toluene, ortho-chloro toluene, C1-C14 aliphatic hydrocarbon and any mixture thereof.

11. The method as claimed in claim 6, wherein the reaction mixture containing the precursor, titanium halide and an electron donating species is heated to 100° C. within 15 minutes and the temperature is kept constant for about 30 minutes.

12. A supported Ziegler-Natta catalyst with controlled morphology that is essentially devoid of iodine prepared in accordance with the method as claimed in claim 6.

13. The supported Ziegler-Natta catalyst with controlled morphology as claimed in claim 12, wherein the sphericity value of the catalyst is in the range of 0.80 to 0.90.

14. The supported Ziegler-Natta catalyst with controlled morphology as claimed in claim 12, wherein the particle breakage index of the catalyst is in the range of 0.85 to 0.97.

* * * * *